(12) United States Patent
Jordan et al.

(10) Patent No.: US 8,100,874 B1
(45) Date of Patent: Jan. 24, 2012

(54) TISSUE REFINING DEVICE

(76) Inventors: Donnell Mark Jordan, North Miami Beach, FL (US); Melbourne Kimsey, II, Danville, CA (US)

( * ) Notice: Subject to any disclaimer, the term of this patent is extended or adjusted under 35 U.S.C. 154(b) by 391 days.

(21) Appl. No.: 12/470,736

(22) Filed: May 22, 2009

(51) Int. Cl.
*A61M 1/00* (2006.01)

(52) U.S. Cl. .......................... 604/319; 604/19; 604/542

(58) Field of Classification Search ............... 604/19, 604/118–121, 317–326, 540–543; 220/500, 220/501, 604, 608, 675, 771, 908; 206/519–520
See application file for complete search history.

(56) References Cited

U.S. PATENT DOCUMENTS

| | | | | |
|---|---|---|---|---|
| 3,680,560 A | * | 8/1972 | Pannier et al. ................ | 604/320 |
| 3,719,197 A | * | 3/1973 | Pannier et al. ................ | 137/205 |
| 3,866,608 A | | 2/1975 | Reynolds et al. | |
| 4,384,580 A | | 5/1983 | Leviton | |
| 4,460,361 A | * | 7/1984 | Nichols ......................... | 604/319 |
| 4,681,571 A | * | 7/1987 | Nehring ........................ | 604/320 |
| 4,809,860 A | | 3/1989 | Allen | |
| 4,820,276 A | | 4/1989 | Moreno | |
| 4,834,703 A | | 5/1989 | Dubrul et al. | |
| 4,870,975 A | | 10/1989 | Cronk et al. | |
| 4,958,557 A | | 9/1990 | Fiala | |
| 5,372,945 A | * | 12/1994 | Alchas et al. ................. | 435/267 |
| 5,397,299 A | * | 3/1995 | Karwoski et al. ............. | 604/6.1 |
| 5,409,833 A | * | 4/1995 | Hu et al. ....................... | 435/297.2 |
| 5,474,675 A | | 12/1995 | Kupka | |
| 5,624,418 A | * | 4/1997 | Shepard ........................ | 604/319 |
| 5,786,207 A | | 7/1998 | Katz et al. | |
| 5,792,126 A | * | 8/1998 | Tribastone et al. ........... | 604/319 |
| 5,795,477 A | | 8/1998 | Herman et al. | |
| 5,807,353 A | | 9/1998 | Schmitz | |
| 5,817,050 A | | 10/1998 | Klein | |
| 5,854,292 A | | 12/1998 | Ailhaud et al. | |
| 6,316,247 B1 | | 11/2001 | Katz et al. | |
| 6,358,474 B1 | | 3/2002 | Dobler et al. | |
| 6,368,310 B1 | | 4/2002 | Bemis et al. | |

(Continued)

FOREIGN PATENT DOCUMENTS

EP 1 462 059 A2 9/2004

OTHER PUBLICATIONS

Web site excerpt dated Jan. 22, 2009 as taken from www.aartinc.net illustrating an implosion proof canister, a fat transfer bottle, and tubing, 3 pgs.

(Continued)

*Primary Examiner* — Tatyana Zalukaeva
*Assistant Examiner* — Benedict L Hanrahan
(74) *Attorney, Agent, or Firm* — Advantage IP Law Firm

(57) ABSTRACT

A device for use in a system or method of collecting and processing aspirated tissue received from a harvesting device is provided by a canister body having a vacuum port and an evacuation port operable to be placed in communication with a vacuum source, a tissue harvesting port for directing tissue into the canister body received from the harvesting device under suction, and a separator element dividing the canister body into an upper vacuum chamber in communication with the vacuum port and the tissue harvesting port and a lower vacuum chamber in communication with the evacuation port, the separator element including a plurality of apertures enabling fluid to pass between the chambers while restricting tissue from doing the same and a depression with a channel leading to a tissue retrieval port to facilitate processed tissue collection.

14 Claims, 12 Drawing Sheets

U.S. PATENT DOCUMENTS

| | | |
|---|---|---|
| 6,623,959 B2 | 9/2003 | Harris |
| 6,918,903 B2 | 7/2005 | Bass |
| 7,153,294 B1 | 12/2006 | Farrow |
| 7,306,740 B2 | 12/2007 | Freund |
| 7,390,484 B2 | 6/2008 | Fraser et al. |
| 7,429,488 B2 | 9/2008 | Fraser et al. |
| 7,469,727 B2 | 12/2008 | Marshall |
| 7,488,312 B2 * | 2/2009 | Rogers et al. ............ 604/406 |
| 2006/0093527 A1 | 5/2006 | Buss |
| 2007/0213666 A1 | 9/2007 | Barzell et al. |
| 2007/0225686 A1 | 9/2007 | Shippert |
| 2008/0057597 A1 | 3/2008 | Freund |
| 2008/0146917 A1 | 6/2008 | Freund |
| 2008/0167613 A1 | 7/2008 | Khouri et al. |
| 2008/0243028 A1 | 10/2008 | Howard et al. |

OTHER PUBLICATIONS

Web site excerpt printed out on May 22, 2009 as taken from product catalog of www.bemishealthcare.com illustrating a Hi-Flow Rigid Suction Canister, 1 pg.

* cited by examiner

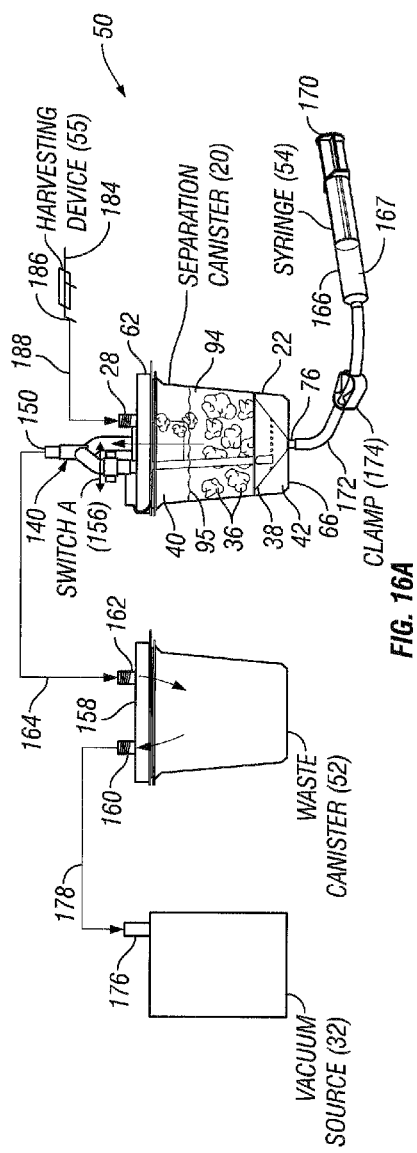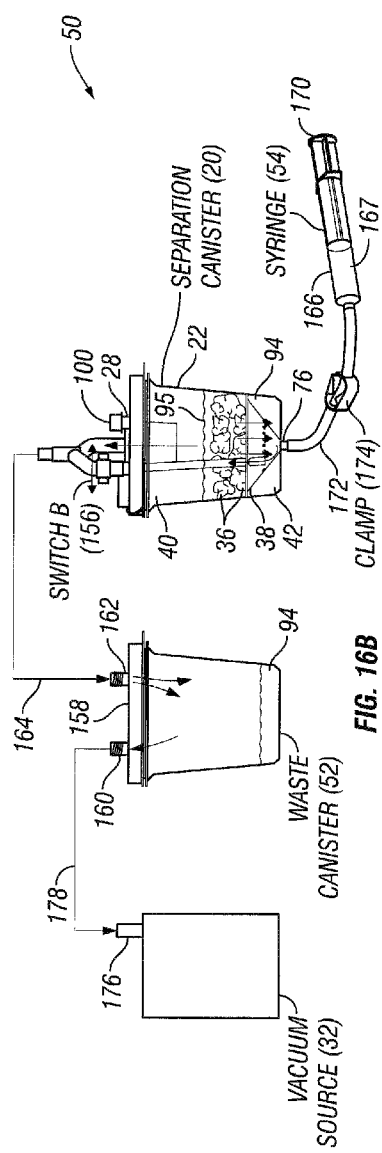

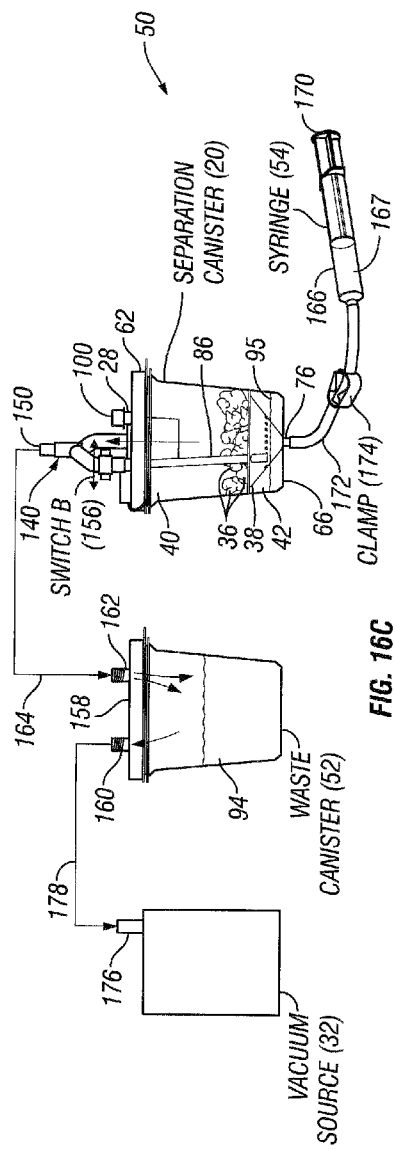
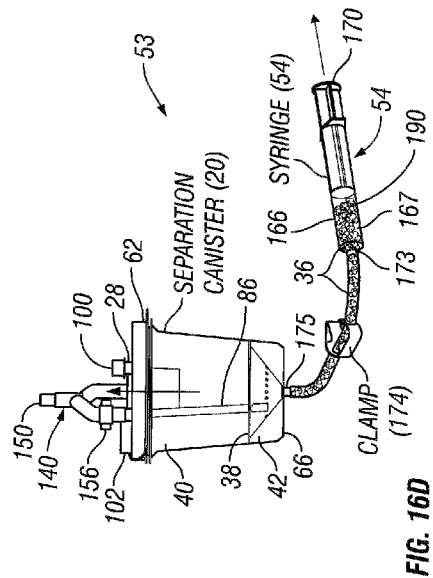
FIG. 16C
FIG. 16D

TISSUE REFINING DEVICE

BACKGROUND

1. Field of the Invention

The present invention relates to fluid and tissue collection devices and more specifically to devices for collecting and processing aspirated adipose tissue for use in autologous adipose tissue implantation procedures.

2. Background Art

Liposuction, a popular type of cosmetic surgery also known as lipoplasty, liposculpture and suction assisted body contouring, is a technique for removing adipose tissue by inserting a hollow tube, or canula, through the skin and connecting it to a vacuum pump to suction out a quantity of fatty tissue. The procedure may be used to remove unwanted deposits of excess fat, to improve body appearance, and to smooth irregular or distorted body shapes, also known as body sculpting. Liposuction may be useful for contouring almost any area of the body including under the chin, neck, cheeks, upper arms, breasts, abdomen, buttocks, hips, thighs, knees, calves, and ankle areas.

A liposuction machine and special instruments are used for this type of surgery. In general, the surgical team first preps the operative site and administers either local or general anesthesia. Through a small skin incision, a suction tube with a sharp end is inserted into the fat pockets and swept through the area where fat is to be removed. The dislodged fat is vacuumed away through the suction tube and deposited into a collection or waste canister. A vacuum pump or a large syringe generates the negative pressure to aspirate the fatty tissue.

In addition to removing unwanted fat, the harvested fat may be re-introduced back into the patient. This is referred to as adipose tissue transplantation. It is preferred to use the patient's own fatty tissue (autologous adipose tissue implantation) since it is more likely to be accepted. Using the patient's own tissues also reduces or even eliminates the need for testing for allergic reactions and the filling replacement tissue may be permanent. Given the decline and drawbacks in the use of foreign substances such as synthetic materials like silicone and teflon as well as the use of foreign tissues such as bovine collagen, and the advantages of autologous adipose tissue, the interest in and demand for this autologous adipose tissue transplantation continues to increase.

Autologous adipose tissue (or fatty tissue) transplantation is performed by many surgeons for various cosmetic and reconstructive procedures, particularly those relating to the face, hands and other areas. More specifically, autologous fat transplantation involves retrieving adipose tissue using liposuction techniques from an area of abundance and then re-injecting the harvested adipose tissue into a different site of the same individual for cosmetic/reconstructive augmentation or enhancement purposes. Generally, prior to the re-introduction of the tissue into the patient, the adipose tissue must be processed or cleaned to maximize the chances of implant survival. Such processing is preferably accomplished while minimizing the exposure of the tissue to air as possible. However, the adipose cells are relatively delicate and the number of steps and length of time required to separate and process the harvested tissue prior to re-introduction into the patient contributes directly to the success of the operation and decreases the likelihood the tissue will be rejected.

The more commonly used aspiration based liposuction techniques include Tumescent Liposuction, Wet and Super-Wet Liposuction, and Power-Assisted Liposuction (PAL). Tumescent liposuction is the most common type of liposuction. It involves injecting a large amount of medicated solution into the areas before the fat is removed. Frequently, the solution may be up to three times the volume of fat to be removed. The fluid is a mixture of local anesthetic such as lidocaine, a drug that contracts the blood vessels such as epinephrine, and an intravenous (IV) salt solution. The lidocaine in the mixture helps to numb the area during and after surgery, and may be the only anesthesia needed for the procedure. The local anesthesia also contributes to the tumescence (swollen and firm) of the target fat. The epinephrine in the solution helps reduce the loss of blood, the amount of bruising, and the amount of swelling from the surgery. The IV solution helps remove the fat more easily and it is suctioned out along with the fat. This type of liposuction generally takes longer than other types. Less blood is also extracted along with the fat over the wet and super-wet techniques.

The wet and super-wet techniques are similar to tumescent liposuction. The difference is that not as much fluid is used during the surgery—the amount of fluid injected is equal to the amount of fat to be removed. This technique takes less time; however, it often requires sedation with an IV or general anesthesia. Surgical blood loss is less for the super-wet technique than the wet technique but still more than the tumescent technique.

Power-assisted liposuction uses an electric variable speed motor to generate a reciprocating motion and move the canula back and forth in a way that mimics the movement made by a surgeon. It decreases the effort required and allows easier fat extraction.

Unfortunately, the nature of liposuction procedures preclude easy tissue isolation after initial harvest, especially on a large scale, because the volume and/or viscosity of the extracted liposuction effluent also contains unwanted components such as oil, blood and anesthetic solution. Currently, there are no standard techniques, methods, or devices that exist for the simple, large scale isolation and refinement of liposuction-harvested adipose tissue. Although a number of specialized canulas, needles and methods for tissue harvest and preparation exist, these techniques are tedious and inefficient. Often, the harvested fat is introduced into a centrifuge further traumatizing the fat and adding more steps to the process before the adipose tissue is re-injected back into the patient. As a result, centrifuge-free processes have been developed.

One example of a centrifuge-less system may be found in U.S. Patent Application Publication No. US2006/0093527 to Buss. In general terms, the Buss harvesting and irrigation device is in the form of a syringe housing open on both ends and constructed to receive a removable filter chamber that slides within the housing. One end of the housing may be coupled to a conventional harvesting canula. The housing may form an airtight chamber for holding a vacuum pressure. The tubular filter chamber includes a porous surface and is supported within the housing and spaced apart from the interior wall of the housing so that fluid may flow freely through the filter chamber and along a space between the outer filter chamber and the inner surface of the housing. The filter is sized to contain a majority of fat cells aspirated into the filter from a lumen in the chamber. Fluids for washing the harvested fat cells may be aspirated through the harvested material and out through the porous material while holding the fat tissues within the filter chamber. While this device does provide some advantages over prior solutions and may be suitable in some situations, there are a significant number of components that must manufactured and assembled to construct the device as well as a considerable amount of personal manipulation of the syringe plunger needed to perform the procedure. This includes several plunger retractions and depressions in order to fully pack fat into the syringe housing and also to draw in irrigation fluids to complete the process. This adds to the complexity of the overall training process as well.

Another example may be found in U.S. Patent Application Publication No. US2007/0225686 to Shippert. In general terms, the Shippert tissue transplantation apparatus includes a collection vessel interconnected to a harvesting canula. The vessel defines a chamber in which a series of tissue collecting syringe bodies are coupled to a manifold also in connection with the harvesting canula to provide multiple filling stations. Each syringe body is perforated to retain fatty tissue in the syringe body while allowing other smaller tissues to exit the syringe body. The chamber is also connected to a vacuum source to draw tissue from the canula into the manifold and on into one or more of the syringe bodies. Under the same vacuum, some of the extraneous tissue is drawn out of the syringe bodies leaving fatty tissue behind.

Once the desired quantity of fatty tissue is collected, a syringe body may be disconnected from the manifold mount. However, an additional sleeve is required to slip over the outer surface of the syringe body to form a sleeve or protective shell and seal before the syringe may be used. Otherwise, the fatty tissue would simply extrude out of the perforated syringe body as the plunger was depressed.

In another variation of the Shippert system, the harvested tissue is first directed into a tissue washing reservoir containing a fluid bath. However, the entry and exit ports are both provided on the lid of the reservoir and, as explained in Shippert, the washing reservoir must be tipped over onto to its side so as to cover the exit port with washed tissue to allow the washed tissue to be suctioned from the tissue washing reservoir into a manifold in communication with the perforated syringe bodies.

Yet another variation described in the Shippert publication reveals the use of a collapsible filter bag within a collapsible collection bag held within the collection canister to receive fatty tissue from the harvesting device. The filter may be used to separate out fatty tissue into the interior of the collection bag from other fluids under suction also introduced into the collection bag. However, in order to access the fatty tissue in the filter bag, the bag must be removed from the canister and the collection bag manipulated to decant unwanted fluids. If washing the tissue is desired, the collection bag is re-introduced into the canister and a fluid additive is added while the bag is massaged by hand to mix and rinse the fatty tissue. Transferring the collected fatty tissue into a syringe involves forcing tissue through an upper port in the collection bag into a syringe body. While providing a useful multi-stage filling station, the number of steps using these Shipped devices results in a cumbersome harvesting and re-injection process that may be improved upon.

While primarily used for tissue specimen collection, another solution for separating tissue may be found in U.S. Pat. No. 5,624,418 to Shepard. In Shepard, a collection and separation device is disclosed that includes a fluid collection container having a lid with a fluid/tissue inlet port and a fluid outlet port that may be coupled to a suction source and a tissue harvesting device. The container also includes a pair of ribs with a lower positioning ledge upon which a pair of tissue collection baskets or traps are positioned above the bottom of the container. While the bottom surface of the container is solid throughout, each basket includes a plurality of fluid flow apertures through which body fluids may pass through while retaining larger tissue specimens in the basket. Fluid collected below the baskets is suctioned up through the fluid outlet port to drain the container, except for the tissue specimens remaining in the baskets. The lid may also be rotated to aligned each basket with the entry port. However, there is no means to access the collected tissue specimens with first removing the lid resulting in an increased exposure to the surrounding air. The baskets may also be removed for further tissue analysis.

Despite these solutions to date, the need remains for an efficient, simple to use, low cost manufacture and assembly tissue collection and processing device that reduces the trauma to harvested tissue, improves the amount of useful tissue, and maintains a sterile processing environment.

SUMMARY

In accordance with the principles of the present invention, a preferred embodiment of a tissue refining device for collecting and processing tissue received from a harvesting device under suction from a vacuum source may comprise a canister body including a vacuum port and an evacuation port operable to be placed in communication with the vacuum source, a tissue harvesting port operable to be placed in communication with the harvesting device and to direct a quantity of tissue retrieved by the harvesting device into the canister body when suction is applied to the vacuum port by the vacuum source, and a tissue retrieval port, and a separator element dividing the canister body into an upper vacuum chamber in communication with the vacuum port and the tissue harvesting port and a lower vacuum chamber in communication with the evacuation port, the separator element including a plurality of apertures projecting through the separator element and a depression with a channel in communication with the tissue retrieval port.

In another feature of the present invention, the separator is in the form of a funnel with a downwardly extending spout extending the tissue retrieval port outside of the canister body and providing an attachment surface for a fat collecting syringe.

In a related feature of the present invention, the evacuation port includes an elongated tube extending from a canister body lid extending through the upper vacuum chamber and through the separator element to dispose an open lower end in the lower vacuum chamber from which fluids may be evacuated.

Another aspect of the present invention is the introduction of a tissue collection syringe and associated tubing coupled to the tissue retrieval port or an extension thereof to facilitate processed tissue collection for re-implantation into a patient site.

Other aspects of the present invention include the introduction of a vacuum and fluid drain manifold coupled to vacuum and evacuation ports of the canister body with the fluid drain portion of the manifold including a drain valve selectively operable to isolate the evacuation port.

In yet another aspect of the present invention, the apertures of the separator elements are positioned at a fixed height within the canister body and a lower end of the evacuation port is disposed in close proximity to the aperture height.

A system for collecting and processing harvested tissue received from a harvesting device under suction using the afore-mentioned canister body placed in series with a waste canister, vacuum source, and harvesting device is also disclosed herein.

A method for collecting and processing harvested tissue received from a harvesting device under suction for subsequent re-introduction into a patient is also disclosed herein.

Other aspects of the present invention will become apparent with further reference to the following drawings and specification.

BRIEF DESCRIPTION OF THE DRAWINGS

FIG. 16A is a schematic diagram of a tissue harvesting, separating, irrigating, and retrieval system in accordance with the principles of the present invention and at an early stage in the harvesting process;

FIG. 16B is a similar view to FIG. 16A further along in the process with the fluid bath partially evacuated;

FIG. 16C is a similar view to FIG. 16B further along in the process with the irrigation process completed; and FIG. 16D is a similar view to FIG. 16C further along in the process with the tissue being retrieved by the attached tissue collecting syringe.

DETAILED DESCRIPTION

Figure 1:
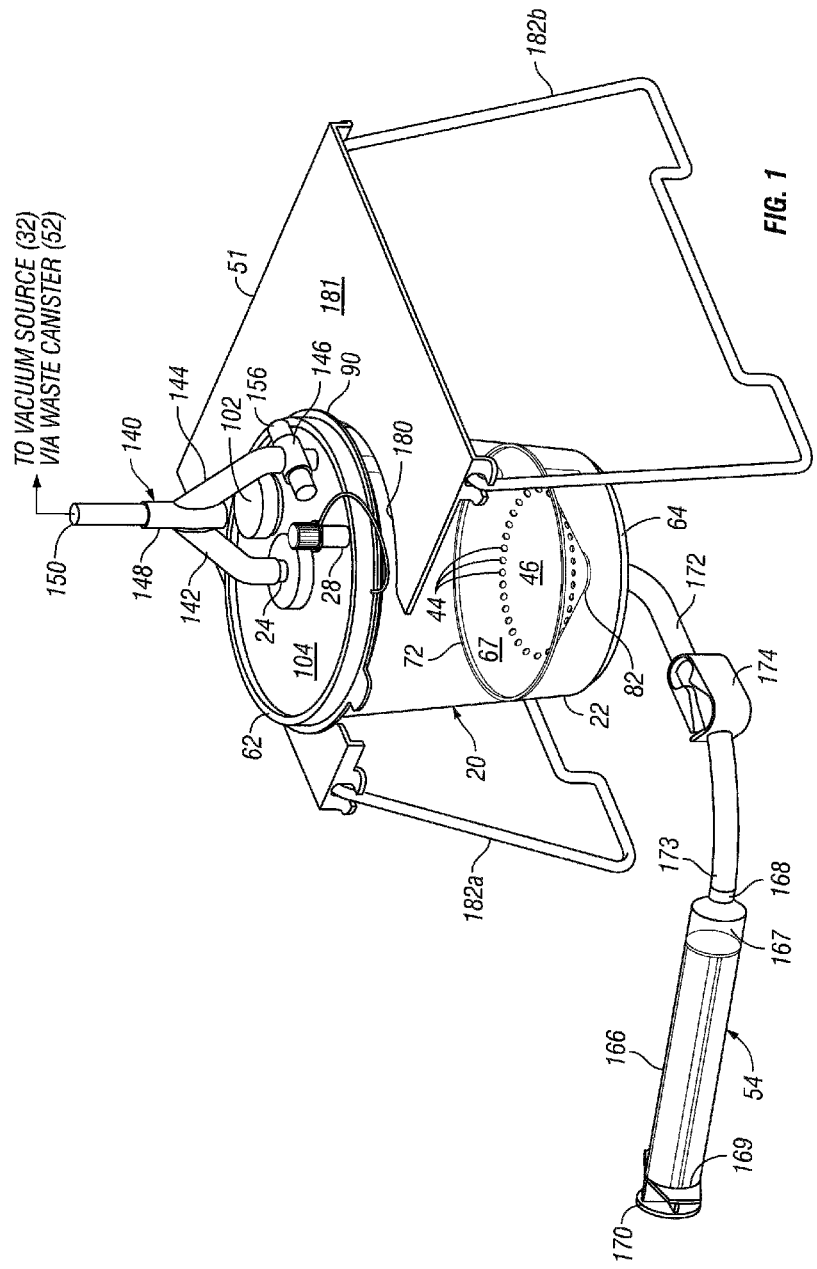
FIG. 1 is an upper right perspective view of an exemplary embodiment of a device for collecting and refining tissue received from a harvesting device in accordance with the principles of the present invention with the device including a partial manifold assembly and being suspended by a holding tray and coupled to a tissue retrieval syringe.
Figure 2:
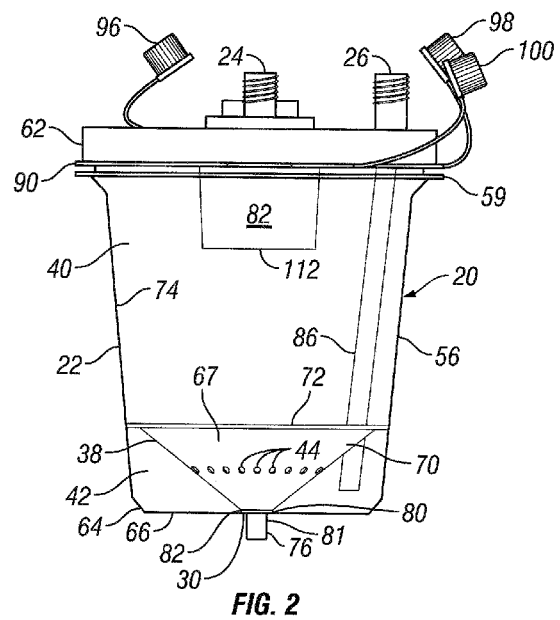
FIG. 2 is a front elevation view of the tissue refining device of FIG. 1, with the manifold removed, in enlarged scale.

Referring now to FIGS. 1-7, an exemplary embodiment of a tissue refining device, generally designated 20, and in accordance with the principles of the present invention, is illustrated. Referring specifically now to the views in FIGS. 1-5, in general terms, the tissue refining device 20 includes a canister body 22 that includes a set of four ports, namely, a vacuum port 24, a fluid evacuation port 26, a tissue harvesting port 28, and a tissue retrieval port 30. The vacuum and fluid evacuation ports may be operatively coupled to one or more vacuum sources 32 (FIGS. 16A-C) while the tissue harvesting port may be operatively coupled to a conventional harvesting device 55 (FIG. 16A) to direct a quantity of tissue 36 (FIGS. 12-15 and 16A-C) retrieved by the harvesting device into the canister body when suction or a negative pressure is applied to the vacuum port by the vacuum source. The tissue refining device also includes a separator element 38 dividing the canister body into an upper vacuum chamber 40 in communication with the vacuum port and the tissue harvesting port and a lower vacuum chamber 42 in communication with the fluid evacuation port. To facilitate the separation process, the separator element may include a plurality of fluid flow apertures 44 projecting through the separator element and a depression 46 with a channel 48 in communication with the tissue retrieval port.

Figure 14:
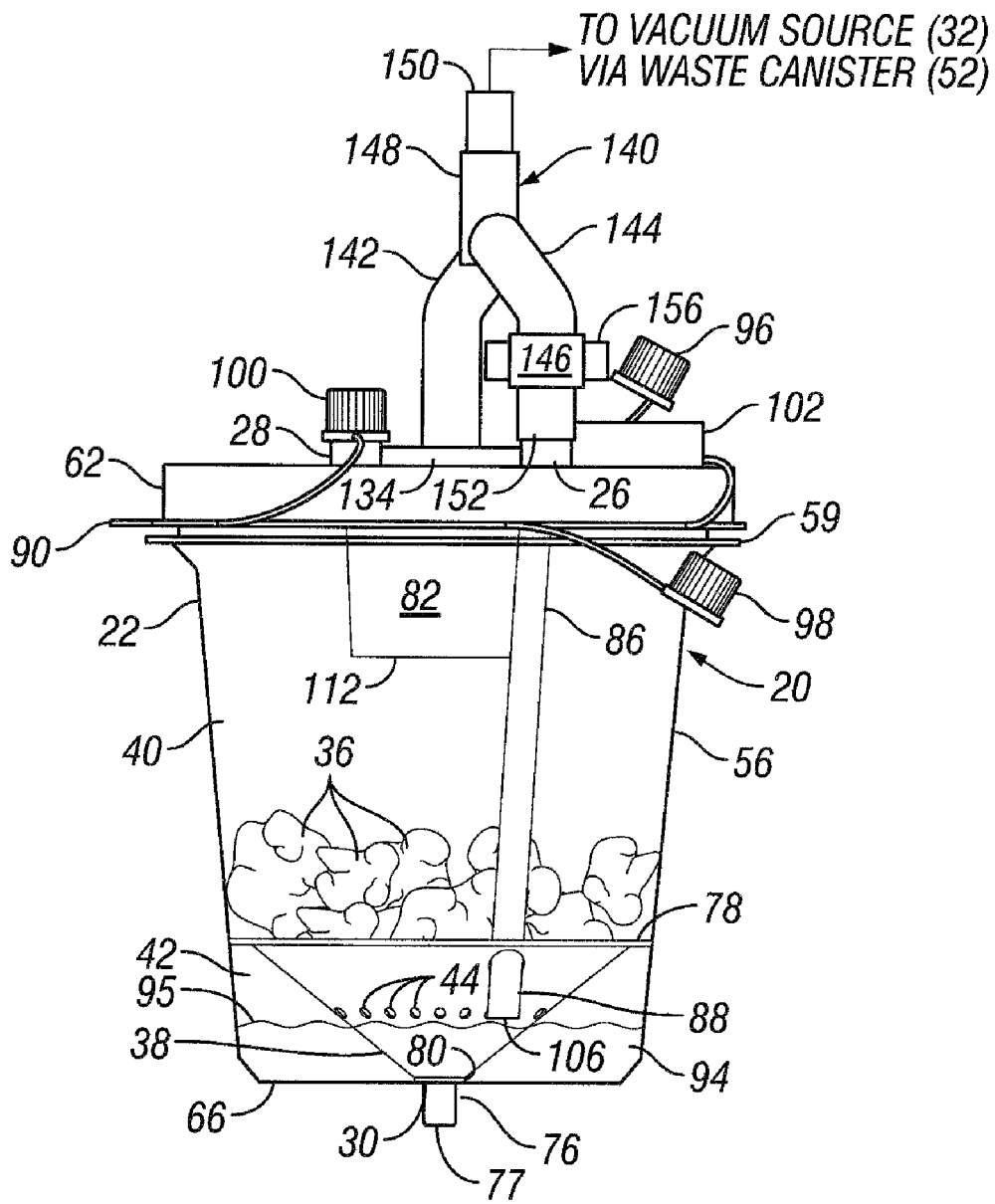
FIG. 14 is a similar view to FIG. 13 further along in the separation and irrigation process.
Figure 15:
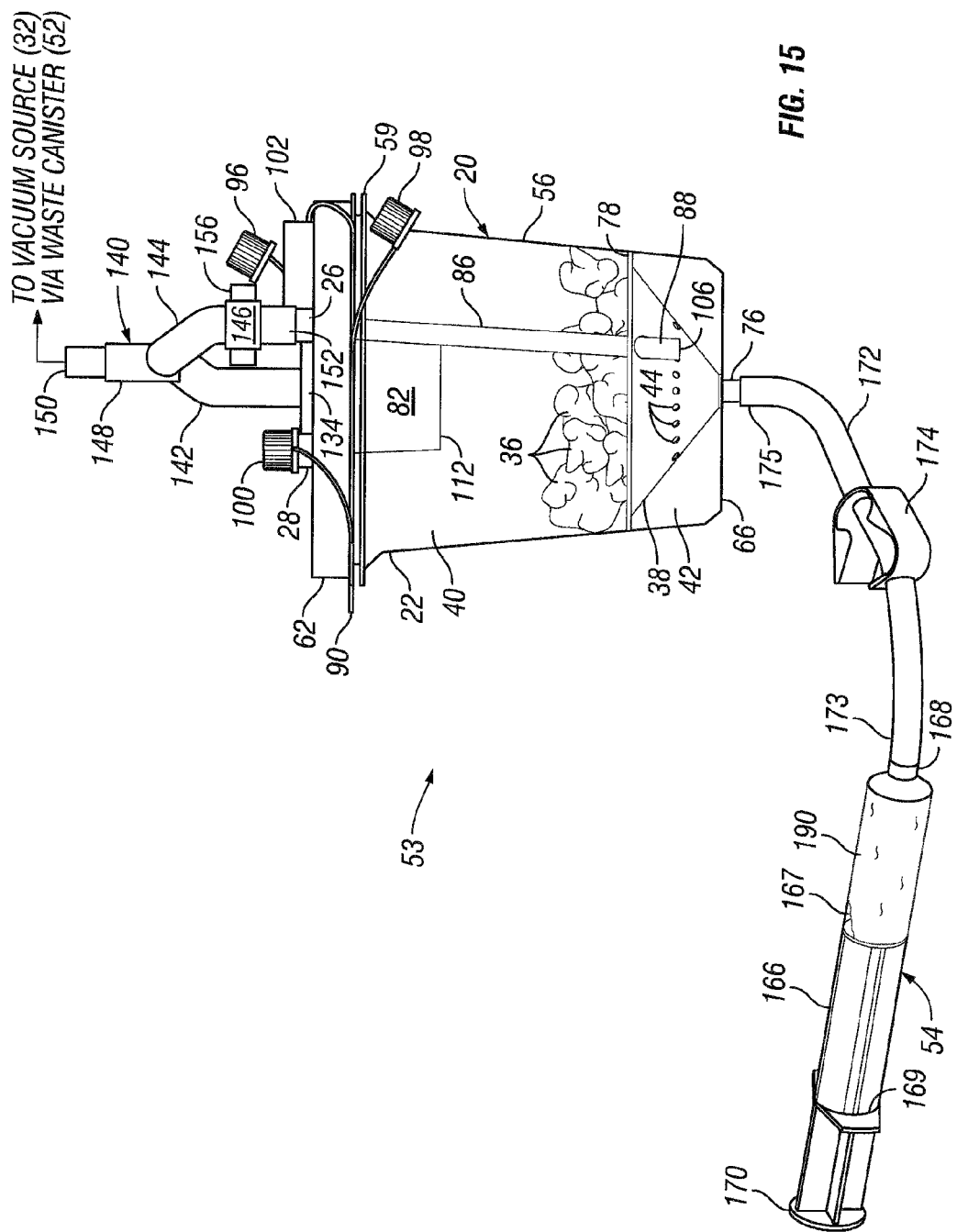
FIG. 15 is a similar view to FIG. 14 with the tissue refining device connected to a tissue retrieval syringe that is partially withdrawn and shows tissue collected in the syringe housing with the pinch clamp open.

The tissue refining device 20, also referred to herein as the separation canister, may also be used as part of a larger tissue harvesting, refining, and retrieval system, generally designated 50, as shown in FIGS. 16A-C or as part of a tissue retrieval subsystem, generally designated 53, as shown in FIGS. 15 and 16D. As will described in more detail below, the separation canister 20, when operatively placed in communication with other components such as the vacuum source 32 (FIGS. 16A-C), a waste canister 52 (FIGS. 16A-C), a collection syringe 54 (FIGS. 1, 15, and 16A-D), and a tissue harvesting device 55 (FIG. 16A) using associated conduits and tubing, may be used as part of a high volume, sterile, closed environment system that facilitates the harvesting of aspirated, adipose tissue, separating such tissue from other collected tumescent fluids, oils, blood, and anesthetics, and processing and treating the harvested fatty tissue with antibacterial solutions and other additives resulting in a quantity of refined fatty tissue for use in autologous adipose transplantation. Pre-loading of the separation canister with a fluid bath 94 (FIGS. 12-14 and 16A-C) as described below may also be used to further reduce the trauma to the harvested tissue and contribute to the refining process.

Referring now to FIGS. 1-2, 4-7 and 11, the canister body 22 includes a generally cylindrically shaped sidewall 56 that tapers outwardly from the bottom to the top and that terminates in an upper rim 58 with an outwardly projecting flange 59 surrounding an open topped region 60 that preferably faces upwardly when in use. The rim forms an attachment surface for a removable lid 62 described below. In this exemplary embodiment, the canister body may have a capacity as little as 100 ml on up to 4 L but a 1.2 to 2.0 L canister capacity has been found to be suitable for most autologous adipose tissue re-injection procedures. However, this is not meant to be limiting in any manner and other suitable smaller or larger capacities as dictated by the procedure will occur to one skilled in the art.

The lower end of the sidewall 56 of the canister body 22 transitions into a shoulder 64 and on into a flat bottom section 66 parallel to the top opening 60. Centrally located within the bottom section is located the tissue retrieval port 30 from which the refined tissue 36, as for example shown in FIGS. 15 and 16C, may be obtained. Alternatively, a port extender as described below may be inserted through the orifice created by the tissue retrieval port.

A suitable rigid plastic, implosion-proof, suction canister for modifying in accordance with the principles of the present invention is available from Bemis Company under the Bemis Healthcare brand. The canister is preferably hydrophobic.

With continued reference to FIGS. 1-2 and 3-7, set within the canister body 22 is the separator element 38 that in this exemplary embodiment is in the shape of a funnel. The funnel includes funnel body 67 with an upwardly facing surface 68 and a downwardly facing surface 70, and a circular rim 72 abutting the interior surface 74 (FIGS. 2 and 4-5) of the canister sidewall 56. The funnel body includes an upwardly facing concavity forming the depression 46 (FIGS. 7 and 11) with a centrally positioned and downwardly projecting spout 76 (best viewed in FIGS. 1-2, 4-5, and 12-15) that defines the channel 48 leading to and extending past the tissue retrieval port 30 outside the canister body 22.

In this exemplary embodiment, the funnel spout 76 projects through the tissue retrieval port 30 and extends beyond the base section 66 of the canister body 22 thus effectively creating a port extender for the tissue retrieval port outside the canister body. The port extender 76 may be conveniently coupled to a length of tubing as will be described below. The port extender also terminates in a spout opening 77 that also operates as the tissue retrieval port by providing access to the top surface 68 of the funnel and upper vacuum chamber 40 from beneath the separation canister 20. It will be appreciated that the spout may also terminate at the tissue retrieval port or be recessed within the canister body 22 as long as there is an orifice on the canister body leading to the upper surface 68 of the separator element 38.

With reference now to FIGS. 1-2, 4-5, and 11-15, the funnel 38 spans the diameter of the canister body 22 and effectively forms a perforated seal between the upper and lower vacuum chambers 40 and 42, respectively, when viewed in connection with the fluid flow apertures 44 discussed below. The funnel may be fixed in place within the canister body and by attaching a locking ring 79 (FIG. 6) having a set of teeth or gripping elements to capture the exterior surface 81 (FIGS. 4-5 and 7) of the portion of the spout extending outside the canister body to prevent the funnel from sliding relative to the canister body. In this exemplary embodiment, the upper edge 78 of the funnel is set at a height about the 300 ml mark on a 1.2 L canister or about ¼ the height of the canister off the bottom wall while the lower point 80 of the funnel body 67 leading to the spout 76 resides at or near the interior surface of the base section 66. A pressure seal 82 (FIG. 2) encircling the portion of the separator 38 where the funnel body 67 meets the spout 76 may be used to provide a better seal where the funnel interfaces with the tissue retrieval port 30.

As best shown in FIGS. 1-2, 4-7 and 12-15, concentrically arranged around the central channel 48 is a singular ring of spaced apart fluid flow apertures 44 (also referred to as fenestrations or perforations) that bore completely through the funnel body to allow fluids such as oils, free lipids, tumescent fluids, non-fatty tissues, blood, anesthetic fluids, and saline gathered during the harvesting process or introduced into the canister body 22 to drain from the upper vacuum chamber to the lower vacuum chamber while restricting the passage of adipose tissue. A preferable aperture size of 1.0 mm has been determined to be suitable for the desired flow rate while avoiding clogging issues but other suitable sizes, including, but not limited to an aperture size range of 0.2 mm to 2.0 mm, depending on the tissue being collected, quantity desired, and desired pass through rate without undue clogging will occur to one of ordinary skill in the art. The ring of apertures is set at a fixed height within the canister body and, in this exemplary embodiment, the apertures appear at about the 100 ml mark in a 1.2 L canister and above the top edge of the spout 76 or about half down in the depression 46.

In addition, while a single ring of fixed height apertures 44 is shown in this example, additional rings may be used or the apertures may appear at varying heights throughout the funnel body. Depending on the vacuum strength introduced by the vacuum source 32 (FIGS. 16A-C) in the lower vacuum chamber 42 some of the fatty tissue may pass through or into the apertures. However, clogging is generally avoided since the fatty tissue tends to float in the fluid bath 94 (FIGS. 12-14 and 16A-C) and such fatty tissue only settles onto the funnel once all other rinsing and bilge fluids has been evacuated through the funnel apertures into the lower vacuum chamber 42. While the funnel body 67 is preferably constructed of a rigid material, other suitable materials will occur to one of ordinary skill in the art and the ring of apertures may be provided by a mesh region instead of through bores or a combination thereof. In this exemplary embodiment, there are twenty apertures or fenestrations, however, this is not meant to be limiting in any manner and other suitable numbers of apertures will occur to one of ordinary skill as well. For example, as few as six apertures has been found to be suitable for the washing and straining process. Instead of apertures, slots may be used as well.

Figure 5:
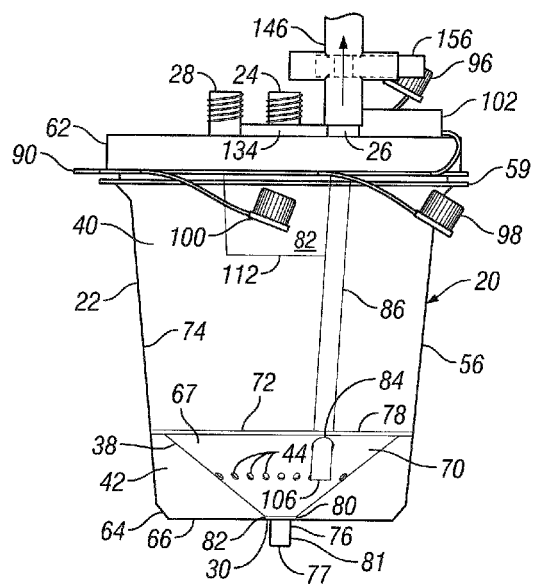
FIG. 5 is a right elevation view of the tissue refining device of FIG. 1, with a portion of the manifold coupled thereto and the switch in an open position, in enlarged scale.
Figure 6:
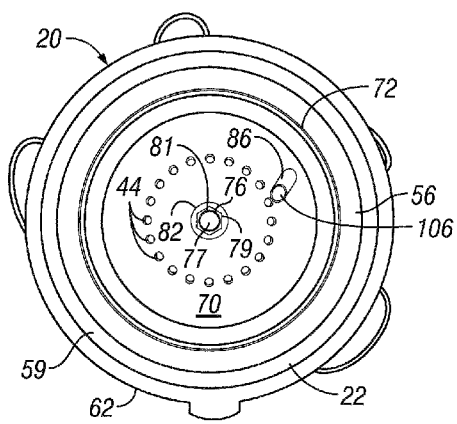
FIG. 6 is bottom view of the tissue refining device of FIG. 1, in enlarged scale.
Figure 7:
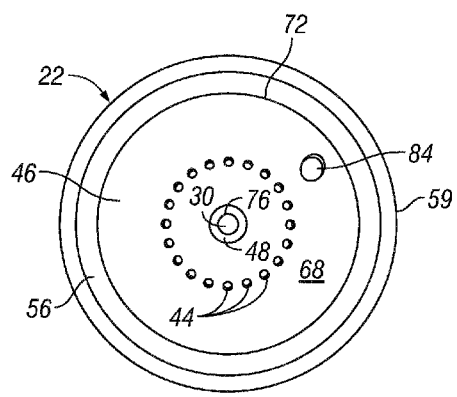
FIG. 7 is a top plan view of the tissue refining device of FIG. 1, in enlarged scale, looking down into the canister body with the lid removed.
Figure 8:
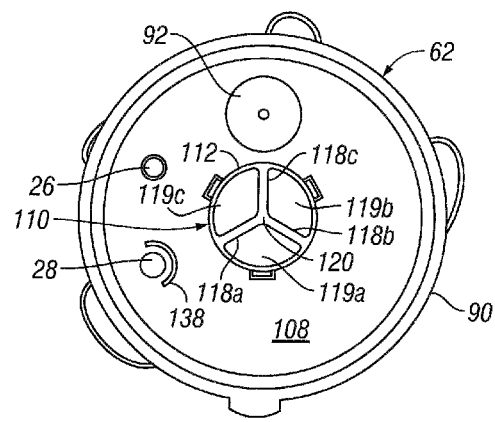
FIG. 8 is a bottom view of the lid of the tissue refining device of FIG. 1, in enlarged scale.
Figure 9:
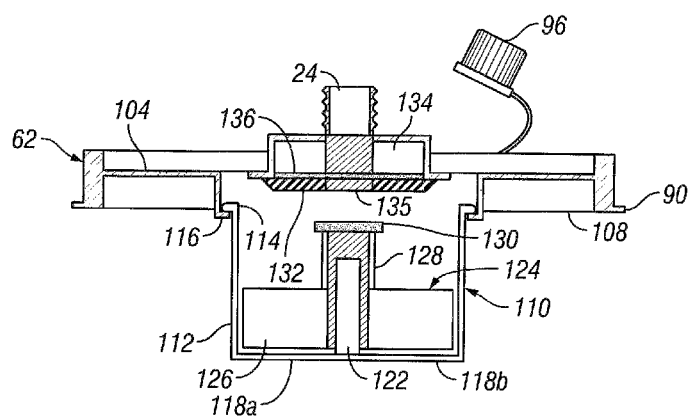
FIG. 9 is an enlarged cutaway view of the valve housing in FIG. 8, illustrating the vacuum port sealing valve and the valve in the open position, with the housing shown in enlarged scale.
Figure 10:
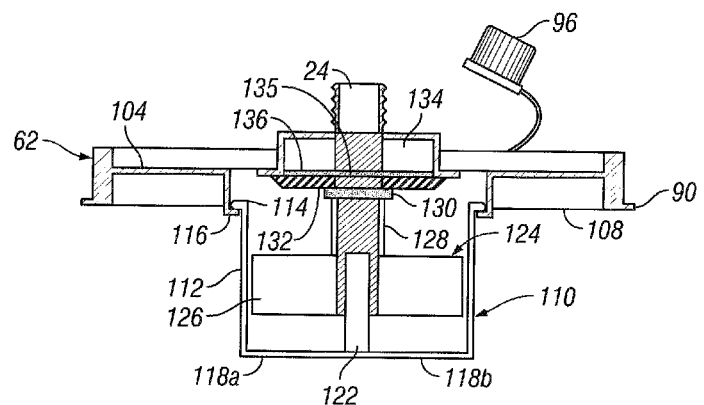
FIG. 10 is a similar view to FIG. 9 with the valve in a closed position.
Figure 11:
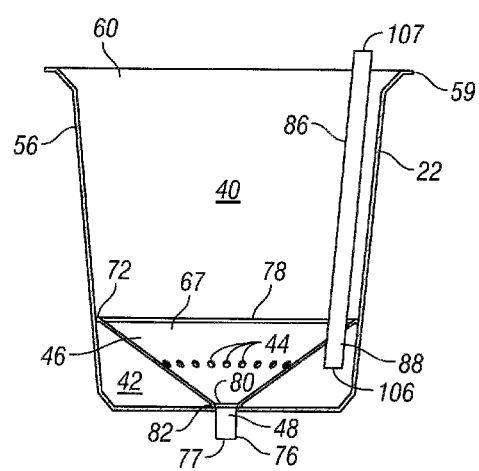
FIG. 11 is a partial cutaway view of the tissue refining device of FIG. 1 with the lid removed, in enlarged scale.

Referring now to FIGS. 5 and 7, the funnel body 67 also includes a pass-through orifice 84 that is enlarged relative to the apertures 44 in this exemplary embodiment. The pass-through orifice facilitates the extension of a hollow drain fluid evacuation tube 86 from the evacuation port 26 through the funnel body to dispose the lower end 88 of the evacuation tube within the lower vacuum chamber 42 or bilge area. This effectively places the evacuation port 26 in communication with the lower vacuum chamber. The fluid evacuation tube effectively provides a port extender for the fluid evacuation port 26 on the lid 62 as described next.

Turning now to FIGS. 1, 3-5, 8, and 12-15, covering the open top 60 of the canister body 22 is a removable, self-sealing lid 62. The substantially flat lid includes a complementary flange 90 for mating with the rim flange 59 to seal off the upper portion of the upper vacuum chamber 40 and further provides access to the vacuum port 24, fluid evacuation port 26, and tissue harvesting port 28 (also referred to as the patient port) as well as an auxiliary enlarged fill port 92 for adding a sterile saline solution or other desired fluid bath 94 (FIGS. 12-14) into the upper vacuum chamber.

Figure 3:
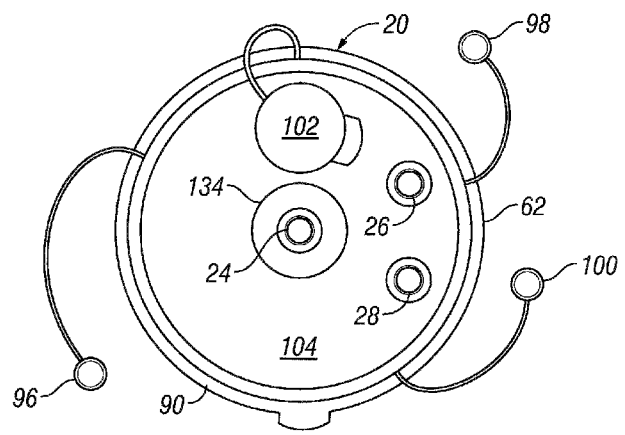
FIG. 3 is a top plan view of the tissue refining device of FIG. 1 with the manifold removed, in enlarged scale.

As shown in FIG. 3, each port 24, 26, 28, and 92 may have a closure cap 96, 98, 100, and 102, respectively, that is also tethered to the lid 62. The caps may be snapped on, screwed on, pressed on, or otherwise suitably engaged with their respective ports. Other suitable closures will occur to one of ordinary skill in the art. The upper surface 104 (FIG. 3) of the lid is substantially flat throughout with each port including an upwardly projecting cylindrical spout or tube to serve as a mounting surface for the corresponding cap. The vacuum port 24, the tissue harvesting port 28, and auxiliary fill port 92 each provide access directly into the upper vacuum chamber 40. Extending downwardly from the fluid evacuation port 26 is the fluid evacuation tube 86 that effectively extends the lower opening of the evacuation port to a lower location 106 in the lower vacuum chamber 42. The top end of the evacuation tube 107 (FIG. 11) may be slip fit onto or into the evacuation port or otherwise suitably secured to the port. The evacuation port 26 and tube 86 may be used to evacuate or drain tumescent fluids, oils, bloods, anesthetics, and other unwanted bilge fluids from the lower vacuum chamber under suction from the vacuum source 32 (FIGS. 16A-C).

Referring now to FIGS. 2 and 8-10, the underside 108 of the lid 62 and positioned beneath the vacuum port is an overflow shutoff valve 110. The overflow shutoff valve includes a cylindrical valve housing 112 with a flange 114 that may be snap fit or screwed into a complementary retention flange 116 projecting from the underside of the lid. The bottom of the housing includes a set of three spokes 118a, 118b, and 118c projecting from a central hub 120 (FIG. 8) to the outer wall of the housing and forming three roughly pie-shaped openings 119a, 119b, and 119c. When viewed in cross-section (FIGS. 9-10), the hub includes a central post 122 projecting up into the valve housing that a float valve 124 may slide up and down on. The float valve includes an enlarged base 126 and a central tube 128 that fits loosely over the post 122 and is capped by a flexible seal 130.

As the float valve 124 rises in response to rising fluid within the upper vacuum chamber 40, the flexible seal 130 may be brought into contact with a gasket 132 covering an enlarged chamber 134 set just beneath the interior of the vacuum port 24 spout. A central opening 135 in the gasket may be closed off by the flexible seal when the float valve encounters rising fluid levels within the upper vacuum chamber 40 that enter the valve housing 112 through the openings 119a-c between the spokes 118a-c in the base of the valve housing as will be explained further below. The float valve acts as a shut off feature to seal off the vacuum port should the fluid levels get too high within the canister body 22. A thin porous paper film 136 may be interposed between the gasket and the entry to the vacuum port to both control the suction force in the upper vacuum chamber and to prevent debris from being sucked into the vacuum port. This film or fibrous wafer contributes to the creation of a vacuum differential between the upper and lower vacuum chambers 40 and 42, respectively during the fluid evacuation process as will be described below. Also, a semi-circular splash guard 138 partially surrounds the entry to the tissue harvesting port 28 on the inside of the lid 62.

Referring to FIGS. 1, 4-5, and 12-15, a vacuum manifold, generally designated 140, may be operatively coupled to the vacuum port 24 and fluid evacuation port 26 for applying a suction force at each port. In this exemplary embodiment, the manifold includes a first branch 142, constructed of ⅜ inch tubing, with one end coupled to the centrally located vacuum port 24 and a second branch 144, constructed of ⅝ inch tubing, with one end coupled to an upper extension of a cross-piece tube 146. The upper ends of both branches flow into a central extension 148 with a free end 150 that may be operatively coupled to the vacuum source 32 (FIGS. 16A-C). The opposing vertical end 152 of the cross-shaped tube may be slipped over or plugged inside the evacuation port 26 to complete the path from the free end of the manifold to the evacuation port. The transverse projecting section 154 of the cross-shaped tube includes a manual drain valve 156 that may be selectively reciprocated from a first position (FIG. 4) blocking the path to the evacuation port 26 to a second position (FIG. 5) clearing the path to the evacuation port 26. Alternatively, a Y-shaped adapter and short segments of tubing may be used to form the manifold.

Turning now to FIGS. 16A-C, a schematic block diagram of the waste canister 52 is shown. A conventional waste canister with a lid 158 having a downstream vacuum port 160 that may be coupled to the vacuum source 32 via a length of tubing 161 and an upstream vacuum port 162 that may be coupled to the free end 150 of the manifold 140 via a length of tubing 164. In this exemplary embodiment, the capacity of the waste canister is preferably greater than or equal the capacity of the separation canister 20. A suitable rigid plastic, implosion-proof, suction waste canister is available from the Bemis Company under the Bemis Healthcare brand. The waste canister is also preferably hydrophobic.

Referring now to FIGS. 1, 15, and 16A-D, the adipose tissue collection syringe 54 may be a conventional syringe with a hollow housing 166 defining a collection chamber 167 having an entry channel 168 on one end that may attach to a canula (not shown) for enabling re-injection of the collected tissue into a patient site or another syringe body. A plunger 170 may be inserted into the enlarged opposing end 169 of the housing and may be reciprocally manipulated within the housing. A conventional 60 cc Toomey syringe has been found to be suitable in this exemplary embodiment but this is not meant to limiting in any manner and other suitable syringe capacities as driven by the procedure and quantity of tissue required will occur to one of ordinary skill in the art.

The syringe 54 may be connected to the lower end of the funnel spout 76 (FIGS. 1-2, 4-5, 12-15, and 16A-D) that extends out the tissue retrieval port 30 using an adipose tissue collection tube 172 having a syringe side end 173 and an opposing spout side end 175. A pinch clamp 174 may be used to slip over the tubing to selectively open and close off the tubing path. When the pinch clamp is open, the syringe collection chamber 167 is placed in communication with the upwardly facing surface 68 of the funnel 38 via the tissue collection tube 172 and channel 48.

Referring to FIGS. 16A-C, the vacuum source 32 (also referred to as a vacuum pump, suction pump, or aspirator) is a vacuum device having a primary vacuum port 176 that may be operatively connected to the downstream port 160 of the waste canister via a suitable length of tubing or conduit 178. A conventional vacuum source, available from MD Resource in Danville, Calif., and having a typical operating range from 1-29 inches Hg has been found to be suitable to both harvest fatty tissue through the conventional canula 55 (FIG. 16A) and withdraw fluid bath and bilge fluid 94 (FIGS. 12-14) from the lower vacuum chamber 42 of the canister body 22 into the waste canister 52. In this exemplary embodiment, it is preferred that the vacuum source be selectively operable to induce a pressure vacuum in a controlled manner to a range of 15-20 inches Hg to perform the procedure but other suitable pressure readings will occur to one of ordinary skill in the art.

Referring now to FIG. 1, as it is preferred to hold the separation canister 20 in an upright orientation during the procedure, a stainless steel holding tray 51 may be provided having a cutout 180 in a holding platform 181 sized to receive and suspend the bottom surface 66 of the canister body 22 up off a lower support surface (not shown) with a pair of folding legs 182. It will be appreciated that the legs of the tray, when extended, are of a sufficient length to suspend the canister 20 off an underlying support surface. Alternatively, the canister body may include a hanger (like for a paint bucket) and be suspended from a hanger tree during use and/or storage.

The harvesting device, generally designated 55, as schematically represented in FIG. 16A, is a conventional harvesting device having a selected canula 184 and a port 186 for coupling to a vacuum hose 188 that may in turn be connected to the tissue harvesting port 28 for directing tissue from the patient site and gathered in the canula to the tissue harvesting port and on into the upper vacuum chamber 40 of the canister body 22 during the harvesting process as will be explained below. A suitable harvesting canula for liposuction techniques and coupling to the separation canister 20 is also available from MD Resource, however, the choice of device and canula size are left up to the surgeon as determined by the procedure.

All tubing and conduits described herein are preferably constructed from rigid or flexible silicone or PVC plastic tubing capable of withstanding the negative pressures introduced into the system without collapsing. The separation canister 20, associated tubing and conduits 164, 172, 178, 188, the evacuation tube 86, and separator element 38, and manifold 140 are also preferably constructed of a transparent or translucent material to facilitate observation of the process by the surgeon. The rigid plastics of the canisters, funnel, lid and rigid plastic tubes may be formed using conventional blow or injection molding techniques, extrusion, or other suitable plastic shaping and forming techniques. The vacuum source 32, waste canister 52, collection syringe 54, and harvesting device 55 are conventional off the shelf components readily available in the liposuction industry. The stainless steel holding tray 51 may be stamped, pressed, or bent using conventional metal shaping techniques.

To facilitate the understanding of the operation of the tissue refining device 20 and associated system 50, turn now to FIGS. 1, 12-15, and 16A-D. The main components 20, 32, 51, 52, 54, and 55 of the system 50 and subsystem 53 for harvesting, refining, and collecting adipose tissue for autologous tissue transplantation may be operatively assembled together in series using the corresponding connective tubing or conduits 178, 164, and 188. In this exemplary process, refining refers to performing one or more of the collection, separation, irrigation, and treatment processes on the harvested fatty tissue prior to re-introduction into the patient.

Figure 4:
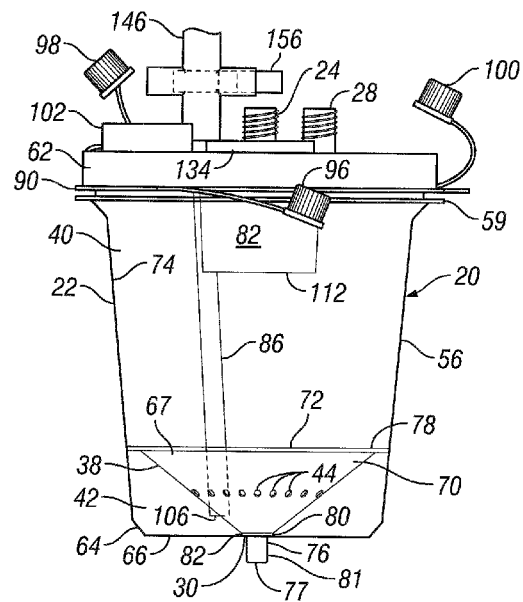
FIG. 4 is a left elevation view of the tissue refining device of FIG. 1, with a portion of the manifold coupled thereto and the switch in a closed position, in enlarged scale.

Within this process description, it is assumed that the respective branches, 142 and 144 of the manifold 140 are already connected to the corresponding vacuum port 24 and evacuation port 26 on the lid 62 and has one free end 150 as shown in FIGS. 12-15. The drain valve 156 is also interposed between the evacuation port 26 and the second branch 144 of the manifold and in the closed position as shown in FIG. 4. It is further assumed that the separator 38 is fixed in place within the canister body 22 to separate the upper vacuum chamber 40 from the lower vacuum chamber 42 and the funnel spout 76 extends out through the tissue harvesting port 30 on the base section 66 of the canister body as shown in FIGS. 1-2, 4-5, 12-15, and 16A-D. The lid 158 of the waste canister 52 is also understood to be in place with the downstream vacuum port 160 and upstream vacuum port 162 uncapped or otherwise exposed. The evacuation tube 86 is also coupled to the evacuation port 26 of the lid 62 as shown in FIG. 5 for example.

As shown in FIG. 1, a surgeon (or surgeon's assistant) may place the separation canister 20 in the cutout 180 of the holding tray 51 having its legs 118a, 118b extended to hold the canister body 22 in an upright configuration with the upper vacuum chamber 40 vertically aligned with, having a common central axis, and disposed above the lower vacuum chamber 42. The upper flange 59 of the canister body 22 resting on the tray surface 181 ensures the separation canister does not pass through the cutout and instead remains with its base section 66 suspended off a lower support surface.

Referring now to FIGS. 2-5 and 12-15, the lid 62 may be placed on the canister body 22 by the surgeon to seal off the top open end 60 (FIG. 11) of the canister body and dispose the lower end 88 of the fluid evacuation tube 86 through the orifice 84 in the funnel body 67 and within the lower vacuum chamber 42 so that the lowermost opening 106 is disposed above, at the same height, or beneath the height of the apertures (aperture line) and above the base section 66 of the canister body 22. Various evacuation tube heights, for example, are shown in FIGS. 2, 4-5, and 12-15. The variation of the height of the lower end of the evacuation tube will vary the point at which a vacuum break forms and the drain fluid is no longer evacuated from the lower vacuum chamber 42 or bilge area. The caps 96, 98, 100, and 102 may be removed from their respective ports 24, 26, 28, and 92 by the surgeon. The drain valve 156 may be slid to the closed position (position A in FIG. 17A and as shown in FIG. 4), if not already in such position to isolate the evacuation port 26 from the vacuum source 32 when the vacuum source or suction pump is later activated.

Referring to FIGS. 1, 15, and 16A, the canister-side end 175 of a fat collection tube 172 may be coupled to the funnel spout 76 of the canister body 22 by the surgeon. The pinch clamp 174 may be slid over the free end 173 of the fat collection tube and pinched to close off the fat collection tube as in FIGS. 1 and 16A-C. The syringe-side end 173 of the fat collection tube may then be connected to the port 168 of the Toomey fat collection syringe 54. The places the fat collection syringe in communication with the upper vacuum chamber 40 of the canister body 22, although the path is closed by the pinch at this point in the process.

Referring to FIGS. 16A-C, the waste canister 52 may also be placed on a flat surface or side by side with the separation canister in a similar holding tray 51. The free end 150 of the manifold may be operatively connected to the upstream vacuum port 162 of the waste canister 52 using the conduit 164. This places the separation canister 22 in series with the waste canister 52. The downstream vacuum port 160 of the waste canister 52 may be connected to the vacuum source port 176 of the vacuum pump 32 with another length of vacuum tubing 178. If necessary, the vacuum pump is plugged into a power source but not yet activated.

Still referring to FIGS. 16A-C, a free end of a length of fat harvesting tubing 188 is coupled to the tissue harvesting port 28 (patient side port) on top of the lid 62. The opposing free end of the fat harvesting tubing is coupled to a conventional fat harvesting device 55 having a canula attachment 184 for retrieving fatty tissue from the patient site. With the tissue harvesting device 55 now in place, it will be appreciated that the vacuum source 32, waste canister 52, separation canister 20, and tissue harvesting device 55 are connected in series as illustrated in FIG. 16A to begin the process.

The fill port cap 102 (FIGS. 1 and 3) of the enlarged fill port 92 on the lid 62 may be removed by the surgeon and an optional fluid bath 94, such as sterile saline or Ringer's lactate solution, may be poured into the canister to fill the canister up to a desired fill line above the upper edge 72 of the funnel. In this exemplary process, the fluid bath 94 fills the lower vacuum chamber 42 beneath the separator 38 and fills up a portion of the upper vacuum chamber 40 so that the upper fluid line 95 is above the funnel rim 72. This pre-loads the canister with about 400 ml or more of sterile fluid bath. It is preferable to ensure the ratio of fluid bath to harvested fat is in favor of the fluid bath allowing the fatty tissue to float initiating the separation process. Other treatments such as antibiotics and/or sterile tissue washing and separation fluids may also be introduced at this time or later on in the process through the fill port 92 as the surgeon determines. Such refining fluids may be introduced for a period of time or incrementally as the surgeon sees fit to wash, separate, and treat the harvested tissue 36. The fill port cap 102 is then placed back on the fill port 92.

At this point, the fill port 92 is capped, the vacuum port 24 and evacuation port 26 are in communication with the vacuum source 32, although the evacuation port is isolated due to the closure of the drain valve 156, the tissue harvesting port 28 is connected to the harvesting device 55, and the tissue retrieval port 30 is coupled to the syringe 54 that is also closed off by the pinch clamp 174 as shown in FIG. 16A. This arrangement presents a pathway from the harvesting device 55 into the upper vacuum chamber 40 through the harvesting tube 188 and patient port 28. There is also a path from the tissue harvesting port 28 to the vacuum port 24 through the upper vacuum chamber 40 of the separation canister 20. There is also a clear path from the primary vacuum port 176 on the vacuum source 32 to the downstream vacuum port 160 of the waste canister 52 via the vacuum tubing 178. The vacuum path continues through the upstream vacuum port 162 of the waste canister 52 through the vacuum tube 164 to the manifold 140 and onto the vacuum port 24 on the lid 62 of the separation canister 20.

Referring now to FIGS. 1, 12-15, and 16A-C, the vacuum source 32 may be turned on by the surgeon and the pump allowed to build to a suitable vacuum (negative) pressure to perform the fatty tissue 36 harvesting process with the harvesting device 55 using conventional harvesting techniques. The overflow shutoff valve 110 is not responsive to the suction force initiated by the activation of the vacuum pump 32 and the vacuum port 24 remains open. With the vacuum source activated, a vacuum pressure relative to the ambient pressure will be generated and maintained in the upper vacuum chamber 40. A vacuum pressure range of 15-20 inches Hg has been found suitable to maintain a sufficient suction force in the upper vacuum chamber 40 to provide sufficient suction to the harvesting device 55 for aspirating fatty tissue 36 from the patient and into the separation canister 20. It will be appreciated that the fluid bath 94 will not exit the upper vacuum chamber with the vacuum seal closed. In addition, no fluid is evacuated through the evacuation tube 86 as the drain valve 156 has isolated the evacuation port 26 from the vacuum source 32 at this point.

Figure 12:
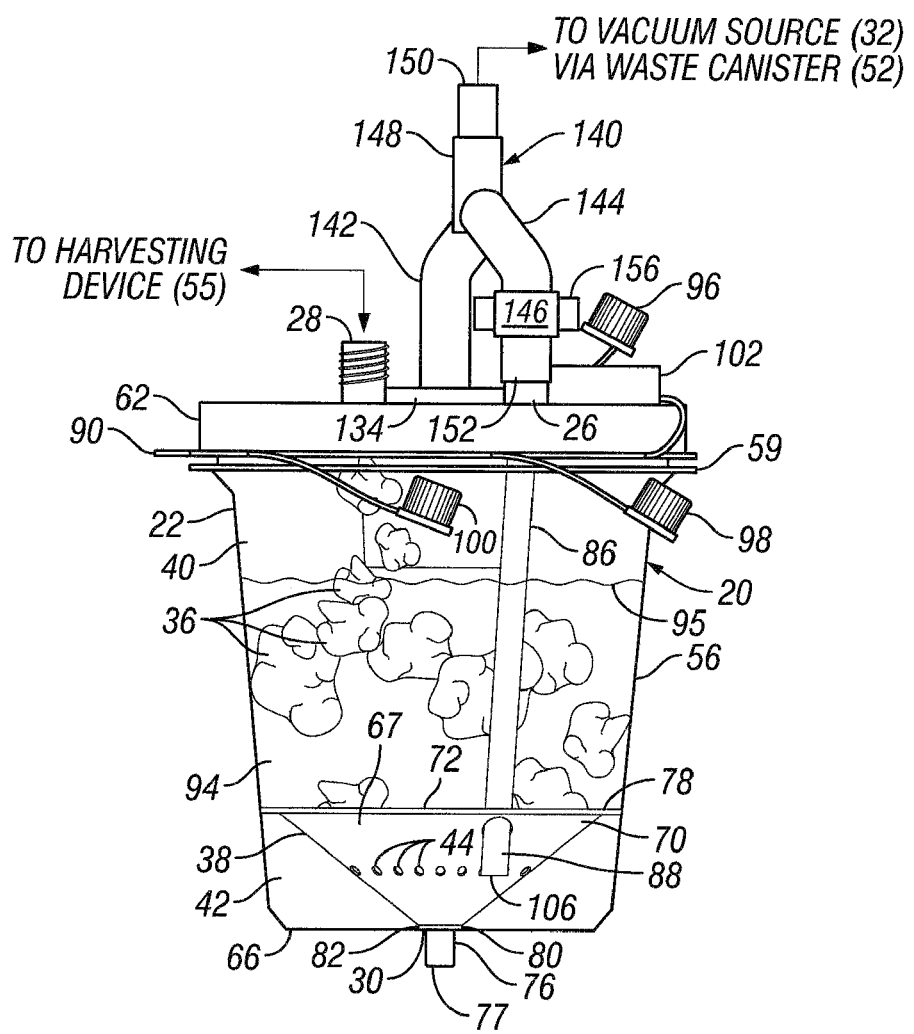
FIG. 12 is a similar view to FIG. 5 with a portion of the vacuum manifold attached and including a fluid bath and fatty tissue at an early stage in the harvesting process.

Using conventional liposuction techniques, the canula 184 of the harvesting device 55 may be inserted into a patient site and a quantity of fatty tissue 36 harvested under vacuum. The fatty tissue will travel through the fat harvesting tube 188 and is directed through the tissue harvesting port 28 to fall into the fluid bath 94 in the upper vacuum chamber 40 of the separation canister 20 as shown in FIGS. 12 and 16A. As commonly occurs during the adipose tissue aspiration process, other fluids and tissues such as blood, anesthetic, collagen strands, infiltrated tumescent fluids, oils, and other non-fatty tissues and fluids may be aspirated along with the fatty tissue. It will be appreciated that the process of separating the fatty tissue from other fluids and non-fatty tissue and fluids begins immediately. While the fatty tissue may initially sink as it is introduced into the fluid bath, the more buoyant fatty tissue tends to rise within the fluid bath and will ultimately float at or near the upper water line 95 of the fluid bath. It will be appreciated that pre-loading the canister body 22 with a fluid bath 94 also cushions the entry of the fatty tissue into the canister thus reducing the trauma to the tissue as well as irrigating the tissue. As the fluid bath 94 mixes with the aspirated tissues, it becomes bilge fluid that will later be evacuated further on in the procedure.

Once enough fatty tissue 36 is collected as determined by the surgeon or surgeon's assistant to complete the transplantation or re-injection procedure, the vacuum source 32 may be left on at the same pressure reading or reduced at this point. As a back up, the overflow shut off valve 110 will seal off the vacuum port 24 should the fluid level 95 within the upper vacuum chamber rise sufficiently and enter the openings 119a-c between the spokes 118a-c of the shutoff valve housing 112 to force the seal 130 on the top of the float valve 124 to close off the central opening 135 of the gasket 132. Should this occur, the vacuum port 24 will be sealed off and no more fluids will enter the canister body 22 through the harvesting port 28. However, it is preferable to turn off the vacuum source while the fatty tissue sits in the fluid bath 94 for a short interval as discussed below. The fat harvesting tube 188 and associated harvesting device 55 may also be disconnected from the lid 62 by the surgeon by removing the harvesting device-side end of the tissue harvesting tube from the tissue harvesting port 28. The harvesting port may be closed temporarily but should preferably remain open during the fluid evacuation process described below. Alternatively, the fat harvesting device 55 may be removed from the harvesting device-side end of the fat harvesting tube and the fat harvesting tube may be closed off using a pinch clamp similar to the pinch clamp 174 on the fat collection tube 172 and then later opened up for the fluid evacuation process. Another alternative would be to introduce an open/close valve into the fat harvesting port 28 or harvesting tube 188 for similar operation to the pinch clamp.

Figure 13:
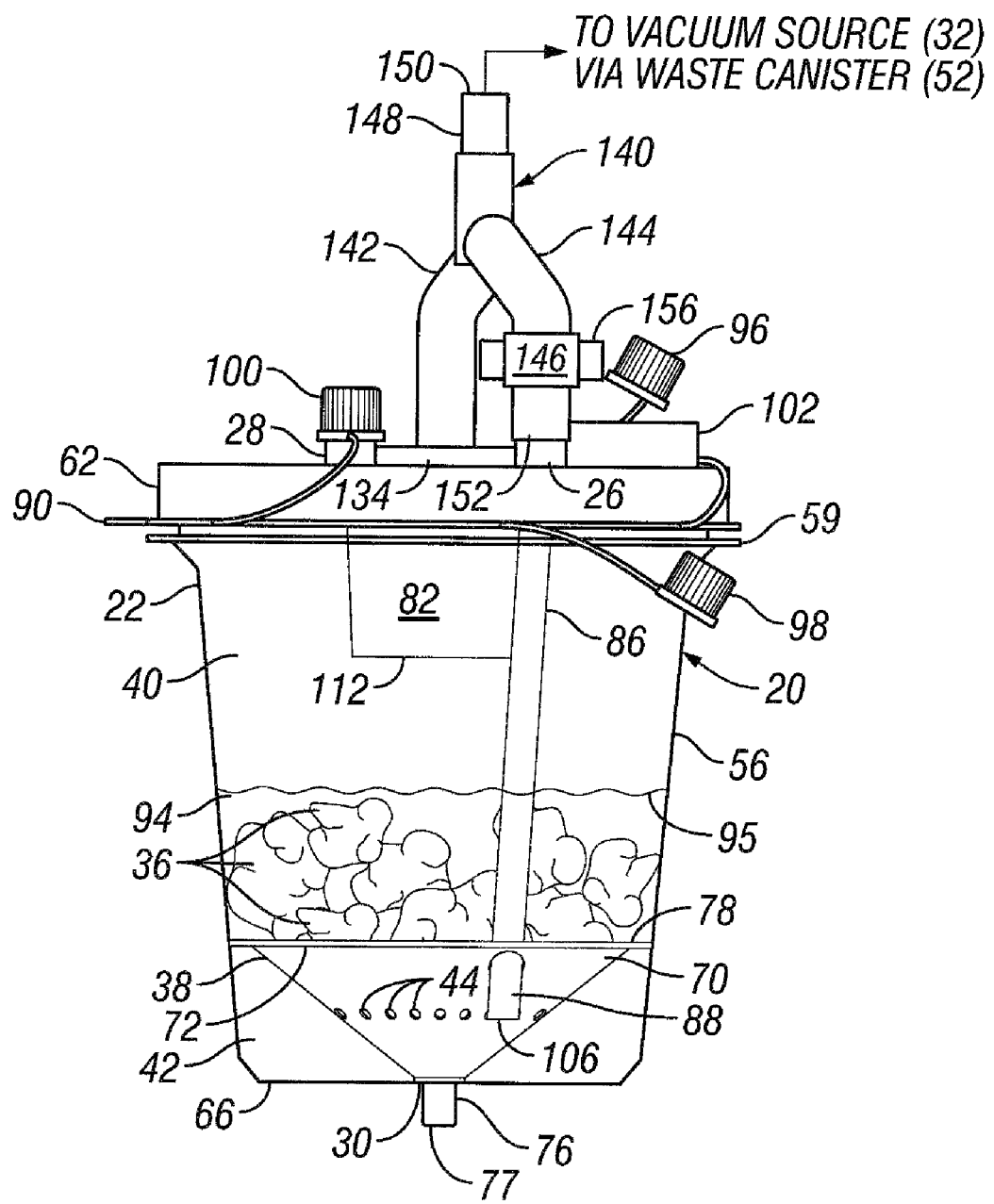
FIG. 13 is a similar view to FIG. 12 further along in the separation and irrigation process.

As shown in FIGS. 12-13 and 16B, at this point, the fatty tissue 36 may be allowed to sit in the fluid bath 94 for several additional minutes, if desired, further allowing the fatty tissue to separate from other harvested fluids and tissues due to its buoyancy to further facilitate the separation process. While shown as slightly settled in the fluid bath 94 in the figures, the fatty tissue 36 generally floats at or near the top surface 95 of the fluid bath.

Assuming the vacuum source 32 was turned off in the prior step, once a desired degree of buoyancy separation takes place, the surgeon may then turn the vacuum source 32 back on and bring the pressure reading back to a range of 15-20 inches Hg suction force reading, although a lower suitable suction pressure may be used depending on the evacuation speed desired. The surgeon may uncap the harvest port 28, if necessary, and also slide the reciprocal drain valve 156 to the open position B (FIG. 16B and as shown in FIG. 5) thus placing the lower vacuum chamber 42 in direct communication with the vacuum source 32 via the waste canister 52 through the associated tubing 164 and 178. It will be appreciated that the drain valve may be opened before the vacuum source activation. If the vacuum source was left running during the prior step, the operating setting for the fluid evacuation process may be brought back to a range of 15-20 inches Hg, if not already at that setting. The opening of the drain valve also switches the primary vacuum force from the upper vacuum chamber 40 to the lower vacuum chamber 42.

With the vacuum source 32 operating at the desired pressure reading and the drain valve 156 open, the irrigation and separation processes continue. As the bilge fluid 94 (fluid bath and other non-fatty tissue) passes from the upper vacuum chamber 40 through the apertures 44 in the funnel 38, the bilge fluid accumulates in the bilge area or lower vacuum chamber 42. A pressure differential, created by the fibrous wafer 136 between the vacuum port 24 and the upper vacuum chamber 40, may occur between the upper and lower vacuum chambers 40 and 42, respectively, in favor of the lower vacuum chamber as some suction is applied to both chambers by the common vacuum source 32. Applying some vacuum to the upper vacuum chamber allows for better control of the fluid evacuation process. Even with a relatively weak pressure differential, the pressure differential does assist in controlling a steady rate of evacuation. This approach allows the fluid bath 94 to be drawn from the upper vacuum chamber 40 through the apertures 44 in the funnel 38 and into the lower vacuum chamber. As the fatty tissue 36 typically floats on top of the fluid bath after it has been dunked and rinsed, the fluid bath and other non-fatty tissue may be separated from the fatty tissue and evacuated through the evacuation tube 86. A vacuum setting of 15-20 inches Hg has found to be provide a suitable evacuation rate of bilge fluid 94 from the lower vacuum chamber 42 through the open end 106 of the evacuation tube 86, out through the evacuation port 26 and vacuum tubing 164 leading to the upstream vacuum port 162 of the waste canister 52.

As shown in FIGS. 12-15 and 16A-C, the fatty tissue 36 is also prevented from entering the lower vacuum chamber 42 due to the size of the perforations 44 in the funnel 38. In addition, as the fatty tissue tends to float on the fluid bath 94, it is unlikely to block the apertures 44. Bilge fluid 94, including both saline bath and non-fatty tissues and other fluids collected from the patient during the harvesting procedure, continues to be collected beneath the funnel in the lower vacuum chamber and evacuated under suction.

The bilge fluid 94 is then drawn out through the lower opening 106 of the evacuation tube 86 past the drain valve 156 and through the manifold 140 and on into the waste canister 52 via the vacuum tubing 164 as shown in FIGS. 16B-C. The weight of the bilge fluid ensures it is deposited into the waste canister and not through the downstream vacuum port 160 in the lid 158 of the waste canister and into the vacuum source 32 connected via vacuum tubing 178. A filter in the suction path to the vacuum pump 32 may also be used to prevent debris from entering the vacuum source.

As shown progressively in FIGS. 12-14 and FIGS. 16A-C, the fluid level 95 in the separation canister 20 continues to drop as more and more bilge fluid is evacuated. Once the fluid level drops beneath the lower opening 106 of the evacuation tube 86, a vacuum break is formed and no more fluid is withdrawn from the lower vacuum chamber. It will be appreciated that this feature provides an auto shut off of the bilge water evacuation process and the surgeon may walk away during this draining part of the procedure, if necessary. The depth of the lowermost opening 106 of the evacuation tube 86 determines the shut off point. The further the evacuation tube extends into the lower vacuum chamber 42, the more bilge fluid 94 will be evacuated. In this exemplary embodiment, it is preferred to locate the bottom edge 106 of the evacuation tube 86 at a position slightly higher than the horizontal aperture line formed by the apertures 44 relative to the base section 66 of the canister body 22. However, it will be appreciated that the lower end of the evacuation tube may be placed at the same height or lower height than the aperture line.

At this point, as shown in FIGS. 14-15 and 16C, almost all of the fluid bath 94 in the upper vacuum chamber 40 has been evacuated into the waste canister 52 except for some residual fluid that may remain in the lower region of the depression 46 of the funnel 38 beneath the apertures 44 or below the evacuation tube 86 in the lower vacuum chamber 42. The fatty tissue 36, as it settles into the depression 46, may also cause some of the residual fluid to spill out the apertures and into the lower vacuum chamber separating more of the bilge fluid from the fatty tissue. It will be appreciated that the concave upper surface 68 of the separator element 38 concentrates the fatty tissue 36 about the channel 48 leading to the retrieval port 30 and out the spout opening 77 without any further handling as the fluid bath 94 is evacuated from the upper and lower vacuum chambers 40 and 42, respectively.

Once the bilge water 94 is substantially removed, it will be appreciated that the remaining fatty tissue that settles onto the funnel 38 has already been rinsed by and separated from the saline bath due to buoyancy, then rinsed and separated from the fluid bath 94, other additives, and the non-fatty fluids and tissues under a gentle vacuum, all within a sterile closed environment of the separation canister 20. The remaining refined fatty tissue is heavily concentrated and ready for re-introduction into the patient. The refined fat remains trapped on the top surface 68 of the funnel 38 within the canister body 22. After the initial washing and separation steps, treatment additives such as antibiotics may be added through the fill port 96 to the fatty tissue 36. The washing process may be repeated one or more times as well to further refine the fatty tissue 36.

The vacuum source 32 may then be turned off to release the vacuum in the canister body 22. Also, if desired, the drain valve 156 may be slid to the closed position (FIG. 5) to again isolate the evacuation port 26 from the vacuum source.

Referring now to FIGS. 15 and 16D, the fat collection tube 172 coupled to the funnel spout 76 may contain some remaining bilge fluid 94. The surgeon may open the pinch clamp 174 on the tube 172 and draw back the syringe plunger 170 to draw out any remaining bilge fluid collected in the length of the fat collection tube. The syringe 54 may be decoupled from the syringe-side end 173 of the tube and the excess bilge fluid expelled into the waste canister 52 by depressing the plunger 170.

The plunger 170 of the fat collection syringe 54 may then be pushed back into the syringe chamber 167 and the syringe may be coupled back to the free end 173 of the fat collection tube 172 attached to the funnel port 76. This places the syringe in direct communication with fatty tissue 36 collected on top of the funnel 38.

The plunger 170 of the syringe 54 may then be drawn back to draw fatty tissue 36 from the upwardly facing funnel surface 68 into the syringe collection chamber 167 as shown in FIGS. 15 and 16D. It will be appreciated that the collected fatty tissue 190 (FIG. 15) was obtained without entering or opening the canister body 22. The gently sloping sidewalls of the funnel body 67 and the channel 48 also cooperate to provide a fat retrieval chute directing refined fatty tissue to the collection syringe 54 via the collection tube 172. If more than one syringe is needed, the primary syringe may be uncoupled and additional syringes as needed may be coupled to the tubing end 173 and the collection process repeated to load one or more syringes with irrigated, separated fatty tissue for re-injection.

The syringe 54, now loaded with fatty tissue 36, may be coupled to a desired canula (not shown) by the surgeon, and the fatty tissue re-injected into the patient site using conventional autologous fatty tissue re-injection techniques. The syringe 54 may also load a smaller syringe with the refined fatty tissue for lower volume re-injections if elected by the surgeon.

Any remaining fatty tissue 36 in the separation canister 20 may be stored for future use. The lid ports 24, 26, 28, and 92 may be disconnected and capped off with their corresponding caps 96, 98, 100, and 102. Likewise, the funnel port 76 may be disconnected and capped off using a similar cap or detachable cap. The canister may be stored as necessary. Otherwise, the separation canister 20 along with its separator 38, fluid evacuation manifold 140, and evacuation tube 86 may be discarded properly.

It will be appreciated that the foregoing separation canister 20 and related system 50 and subsystem 53 and method as described herein cooperate to minimize the number of steps required to harvest, refine, and collect the fatty tissue prior to re-introduction into the patient site. In addition, trauma to the tissue, commonly caused by the use of a centrifuge, rougher manipulation of the tissue and tissue container as commonly occurs when directing the tissue against a solid surface, and extending the time of the tissue outside the patient is significantly reduced using the components and methods described herein, all while maintaining a sterile environment. As a result, a higher percentage of viable adipose tissue is made available for transfer while simultaneously reducing the amount of cellular debris that may otherwise commonly re-introduced into the patient along with the fatty tissue. The transparent nature of the separation canister also facilitates a simple visual method for checking the tissue as well. The separation canister also advantageously may easily be integrated with conventional off the shelf waste canisters, vacuum sources, syringes, and harvesting devices.

While the present invention has been described herein in terms of a number of preferred embodiments, it will be appreciated that various changes, uses, and improvements may also be made to the invention without departing from the scope and spirit thereof. Any numbers or ranges are meant to be exemplary and not limiting.

For example, it will be appreciated that multiple separation canisters 32 may be connected in series to harvest larger volumes of tissue 36. In addition, a dedicated vacuum source coupled to a corresponding vacuum port and evacuation port may be used. While this may eliminate the need for a drain valve as the vacuum sources could be operatively turned on and off to control the harvesting and draining processes, such arrangement is generally considered more cumbersome. In addition, while the evacuation port described herein is preferably located in the canister lid, the drain port may appear at other locations on the canister body as long as long as there is access to the bilge area. While the separation canister and related system and method described herein is described in terms of a preferred one-valve system, additional open/closed valves may be used in the other vacuum lines and conduits or built into the other ports as well to isolate or open the vacuum, tissue harvesting, and collection pathways.

It will also be appreciated that by constructing the separation canister from plastic materials instead of the autoclave proof glass materials commonly used for re-usable canisters, additional costs, for both materials and cleaning, may be saved from the introduction of a one-use disposable canister.

What is claimed is:

1. A device for collecting and refining tissue received from a harvesting device under suction from a vacuum source, the apparatus comprising:
   a canister body including a vacuum port and an evacuation port operable to be placed in communication with the vacuum source, a tissue harvesting port operable to be placed in communication with the harvesting device and to direct a quantity of tissue retrieved by the harvesting device into the canister body when suction is applied to the vacuum port by the vacuum source, and a tissue retrieval port;
   a separator element dividing the canister body into an upper vacuum chamber in communication with the vacuum port and the tissue harvesting port and a lower vacuum chamber in communication with the evacuation port, the separator element including a plurality of apertures projecting through the separator element and a depression with a channel in communication with the tissue retrieval port;
   the canister body includes a removable top covering having the vacuum port, the tissue harvesting port, and the evacuation port, and a base including the tissue retrieval port; and
   the evacuation port includes an elongated tube projecting into the canister body from the covering and having a lower end extending through the separator element and disposed within the lower vacuum chamber.

2. The device as set forth in claim 1 wherein:
the separator element includes a perforated funnel body secured within the canister body with the channel being formed by a spout projecting from the lowermost region of the depression in the funnel body and terminating in a lower end in communication with the tissue retrieval port.

3. The device as set forth in claim 1 further comprising:
a vacuum manifold having a free end operable to be coupled with the vacuum source, a first branch in communication with the vacuum port, and a second branch in communication with the evacuation port and having an actuator constructed to selectively isolate the evacuation port from the vacuum source when the manifold is coupled thereto.

4. The device as set forth in claim 1 wherein:
the separator element includes an upper surface with an outer rim positioned within the canister body at a fixed height above a base section of the canister body.

5. The device as set forth in claim 4 wherein:
the evacuation port includes an opening disposed beneath the outer rim of the separator element and within the lower vacuum chamber.

6. The device as set forth in claim 1 further including:
a syringe in communication with the tissue retrieval port and operable to withdraw a selected quantity of tissue settled onto an upper surface of the separator element through the tissue retrieval port.

7. The device as set forth in claim 1 wherein:
the canister body is at least partially filled with a fluid bath with an uppermost fluid line above a top surface of the separator element;
the evacuation port includes an opening at least initially in communication with the fluid bath and constructed to evacuate fluid out of the canister body from the lower vacuum chamber as suction is applied by the vacuum source coupled thereto until the uppermost fluid line is disposed beneath a lowermost edge of the evacuation port opening; and
the vacuum port includes an opening disposed above the uppermost fluid line.

8. The device as set forth in claim 1 further comprising:
a waste canister placed in series with the canister body and including a first port in communication with the vacuum source and a second port in communication with the vacuum port of the canister body.

9. The device as set forth in claim 1 further including:
an overflow valve disposed beneath the vacuum port within the upper vacuum chamber, the overflow valve being responsive to a rising fluid level within the upper vacuum chamber to seal off the vacuum port.

10. The device as set forth in claim 1 further comprising:
a first length of tubing having a first end coupled to the vacuum port and having a free distal end;
a second length of tubing having a first end coupled to the evacuation port and having a free distal end;
a Y-connector having a first branch coupled to the free distal end of the first length of tubing and a second branch coupled to the free distal end of the second length of tubing, and a main line operable to be coupled to the vacuum source to place both the vacuum port and evacuation port in communication with a common vacuum source; and
a drain valve inline with the second length of tubing and being selectively operable to isolate the evacuation port from the vacuum source when coupled thereto.

11. The device as set forth in claim 1 further including:
a holding tray operable to suspend the canister body in an upright position.

12. A system for collecting and refining tissue to be used with a harvesting device and a vacuum source, the system comprising:
- a canister body including a vacuum port, an evacuation port, a tissue harvesting port operable to be placed in communication with the harvesting device and to direct a quantity of tissue retrieved by the harvesting device into the canister body when suction is applied to the vacuum port by the vacuum source, a tissue retrieval port, and a separator element dividing the canister body into an upper vacuum chamber in communication with the vacuum port and the tissue harvesting port and a lower vacuum chamber in communication with the evacuation port, the separator element including a plurality of apertures projecting through the separator element and a depression with a channel in communication with the tissue retrieval port;
- the canister body includes a removable top covering having the vacuum port, the tissue harvesting port, and the evacuation port, and a base including the tissue retrieval port;
- the evacuation port includes an elongated tube projecting into the canister body from the covering and having a lower end extending through the separator element and disposed within the lower vacuum chamber;
- a vacuum source;
- a manifold having a first branch in communication with the vacuum port, a second branch in communication with the evacuation port, and a free common end;
- an evacuation port isolator in communication with the evacuation port and selectively operable to isolate the vacuum source from the evacuation port; and
- a waste canister having a first port in communication with the vacuum source and a second port in communication with the free common end of the manifold.

13. The system as set forth in claim 12 wherein:
the evacuation port includes a lowermost opening to be disposed beneath an uppermost fluid line of the fluid bath introduced into the canister body with evacuation port being operable to cease draining fluid out of the lower vacuum chamber when the uppermost fluid line falls below the lowermost opening.

14. The system as set forth in claim 12 further comprising:
a syringe in communication with the tissue retrieval port and operable to capture a quantity of tissue from an upper surface of the separator element.

\* \* \* \* \*